(12) United States Patent
Ayari et al.

(10) Patent No.: US 9,192,777 B2
(45) Date of Patent: Nov. 24, 2015

(54) SET OF ELECTROMAGNETIC FIELDS HAVING DIAGNOSTIC, PREVENTIVE, THERAPEUTIC AND BIOTECHNOLOGICAL PURPOSES

(76) Inventors: Mohamed Ayari, Pessac (FR); Arthur Balana-Cervero, Pessac (FR)

( * ) Notice: Subject to any disclaimer, the term of this patent is extended or adjusted under 35 U.S.C. 154(b) by 2725 days.

(21) Appl. No.: 10/467,816

(22) PCT Filed: Jan. 25, 2002

(86) PCT No.: PCT/FR02/00325
§ 371 (c)(1),
(2), (4) Date: Aug. 12, 2003

(87) PCT Pub. No.: WO02/062418
PCT Pub. Date: Aug. 15, 2002

(65) Prior Publication Data
US 2007/0161883 A1  Jul. 12, 2007

(30) Foreign Application Priority Data

Feb. 6, 2001 (FR) ..................................... 01 01670

(51) Int. Cl.
*A61N 1/00* (2006.01)
*A61N 5/02* (2006.01)
*A61N 2/00* (2006.01)

(52) U.S. Cl.
CPC . *A61N 5/02* (2013.01); *A61N 2/002* (2013.01)

(58) Field of Classification Search
CPC .......... A61B 5/05; A61B 5/055; A61B 19/00; A61N 1/00; A61N 2/02; A61N 2/00
USPC ......................................... 600/9–15, 407, 410
See application file for complete search history.

(56) References Cited

U.S. PATENT DOCUMENTS

| | | | | |
|---|---|---|---|---|
| 3,773,049 A | * | 11/1973 | Rabichev et al. | 607/1 |
| 5,564,421 A | * | 10/1996 | Ehnholm | 600/410 |
| 6,142,927 A | * | 11/2000 | Clark | 600/9 |
| 6,443,883 B1 | * | 9/2002 | Ostrow et al. | 600/14 |

* cited by examiner

*Primary Examiner* — Christine H Matthews (57) ABSTRACT

Biophysicoclinical process and device to implement it. It initiates the emergence of a clinical approach to pathologies understood and treated within their somatopsychic global nature. The fundamental basis of the process consists in producing and overlaying in a volume of exposure—containing part or whole of a living subject, animal or human being—a magnetic field and one or several very high frequency electromagnetic fields, the latter being essentially angle modulated. The biological effects thus produced are many and varied; they can be observed, in particular, in the stimulation of certain defence systems of the body, such as the intensification and reinforcement of the immune defences.

12 Claims, 6 Drawing Sheets

SET OF ELECTROMAGNETIC FIELDS HAVING DIAGNOSTIC, PREVENTIVE, THERAPEUTIC AND BIOTECHNOLOGICAL PURPOSES

GENESIS OF THE INVENTION

The present invention is in keeping with our reflection and questioning over a long period of time concerning professional practices in the clinical field, and in the fields of biology and physics. This questioning was not simply reduced to the scope and the limits of these practices. It was also, and more particularly, aimed at identifying the principle obstacles which prevent them being put into practice on a significant scale.

These days we are far from a global, holistic approach to the patient, taking the entire person, their life and circumstances, into account; as if it were impossible to restore to the patient a unifying representation of himself. So, to try and overcome the deep seated obstacles preventing the emergence of a pacifying global mediation concerning the patient as a whole, the solution seems to lie in the fundamental rehabilitation of clinical practices.

In Latin, clinicus means "by the bedside of one who suffers."

By placing ourselves right from the start in relation to the patient's suffering, we are describing the ethics on which we have based our multidisciplinary study: to relieve this suffering.

The world of autism and psychosis is undoubtedly one of the most puzzling and complex worlds, but also one which is full of lessons of all sorts. The global face of these particular psychosomatic disorders is indeed quite troubling: troubling because there are disturbing flaws—structural and cultural—in our so-called therapeutic point of view.

It was therefore profound questioning about our practices concerning so-called autistic and psychotic children, that a different clinical point of view emerged.

This encouraged us to listen—in a different way—to the global symptoms in order to better understand (a) what they are based on and (b) to welcome the global re-emergence which has long been held in check.

While the patient is still looking for global mediation, partial mediation, psychological mediation, even if effective, can only partially assist him. Indeed, if for psychological mediation this globality remains unattainable it is because it can have no direct and immediate action on the sommatic apparatus. Based on restricted views, glued exclusively to the psychological, it does not have a specific power to stir the somatic apparatus. Whence the need to develop mediation which would help to stir the somatic apparatus and thus contribute to the emergence of a form of global mediation to assist the patient in his psychosomatic globality.

Having regard for the patient as a whole would lead us to restore a truly pacifying discourse to our words and the functions of mediation to our tools for treatment.

To attempt to work in this direction, we have rooted our mediator—support for somatic mediation—in the clinical field.

On the biophysical level, the basis of our invention is a series of instruments which enables particular electromagnetic fields to be associated in a particular fashion. The object of applying them to a living organism is to emphasize its natural abilities without altering the sommatic apparatus, without generating harmful side effects and without leading to dependence.

These instruments only came to light after in-depth and detailed examination of the scope and the limits of a biophysical lead, provided by Antoine Prioré and his collaborators, the only one as far as we are concerned that is really promising.

We were able to examine in depth the whole of the "Prioré file," a unique source of information consisting of several thousand detailed and abundant pages: scientifique publications, reviews and reports, experiment logs, patents, letters (a considerable number) and private communications, manuscripts and personal notes, press articles, photos and so forth.

The trail revealed that under very subtle and precise methodological conditions, the therapeutic effects of electromagnetic fields are conclusive, diverse and varied, and have no harmless side effects.

The results of the biological experiments undertaken, in particular by the following biologists, doctors, vets or physicists (F. BERLUREAU, M. FOURNIER, J. BIRABEN, G. DELMON, M. R. RIVIÈRE, M. GUÉRIN, R. COURRIER, A. COLONGE, E. J. AMBROSE, R. and A. N. PAUTRIZEL, P. CHATEAUREYNAUD, G. and G. MAYER, A. LWOFF, S. AVRAMEAS, I. CHOUROULINKOV, A. J. BERTEAUD, A. M. BOTTREAU, P. MATTERN, A. CAPBERN, T. BALTZ, M. DALLOCHIO, R. CROCKETT, R. COURTY, G. DUBOURG), over a period of years on animals are spectacular (see Bibliography concerning published works).

Antoine Prioré was the only expert-operator of his own instruments; his collaborators (scientists, biologists, etc) were only there to reap the effects (biological results) of his "Effect." This form of "mutual consent" would lead to a foreseeable but fatal result: he died without divulging the secret of the workings of his machine to those close to him.

Our job was to work at revealing the secret. On the one hand to piece together the mental processes behind the work of this researcher and on the other, to find out the significance and the limits of his remarkable contribution by sorting out the main components: The Prioré machine, The Prioré Effect and The Prioré Therapeutic Effects. Sort them out in order to grasp them better and to subject them to hypotheses which were theoretically and clinically founded.

In conclusion, it turns out that even with Prioré's machines in their final version, it seemed as if the rays just sprang out of a black box whose physical parameters seemed to be barely mastered which could at any time compromise all attempts at optimising the long awaited effects.

On the other hand, our hypotheses, compensating for these shortcomings, have enabled us with current techniques to design a variety of instruments, as varied as there are applications, which can be adjusted according to the various clinical requirements. The project which deals with the treatment of infantile autism—in its psychosomatic globality—will be an eloquent illustration.

The present invention thus concerns a biophysicoclinical process which consists in producing and overlaying in a single volume various electromagnetic fields each of which has quite specific characteristics. The simultaneous association of these fields produces biological effects on a living organism exposed in the volume in vivo, both in animals and in humans. These biological effects, in addition to contributing to obtaining a biological substance, can be used for diagnostic, preventive and therapeutic purposes when used as part of a global psychosomatic clinical approach.

The present document in respect of taking out a patent originates from the full and final version of our paper which details the theoretical, clinical and methodological base for a global clinical approach, signified here by the biophysicoclinical process that is the object of the present invention. This paper and the Prioré File will both be duly published.

PRIOR ART

Previous Work which Inspired Us.

Results of Biological Experiments on this Subject.

The effects of electromagnetic fields on living organisms has been an on-going theme of research. A great majority of these studies has been concerned with the study of eventual harmful effects of electromagnetic fields on organisms. As for ourselves, we became interested in the therapeutic effects of electromagnetic fields. The work of Antoine PRIORE and his collaborators in this field is especially remarkable. This work showed, in particular, that the simultaneous association of particular electromagnetic fields enables significant stimulation, in other words intensifying, of the in vivo immune system, both specific and non specific, in animals subjected to these fields. The healing effects which followed, in the case of a number of diseases, were observed.

To this effect, a number of pathogenic agents were used: grafted tumours—T8 epithelioma, lymphosarcomas LS1, LS2 and 347 (lymphoblastic), fibrosarcoma Sal—, tumours induced by benzopyrene, parasites—Trypanosoma equiperdum, Trypanosoma gambiense, Plasmodium berghei— amongst others. Most of these agents are particularly noted for their great virulence [PAUTRIZEL; RIVIÈRE]; as far as the T8 tumour, in particular, is concerned, Messrs RIVIÈRE and GUÉRIN emphasized that until then no means of chemistry or physics (X rays, for example) had been able to overcome this particular type of tumour [GRAILLE, 1984].

All the control animals not exposed to these electromagnetic fields died within a few days or weeks according to the species and the disease administered.

However, animals exposed to these fields saw the number of blood parasites decrease in the case of parasitosis; for others, tumour formations declined—sometimes significantly—as did metastases, in the case of cancers. When the right conditions were combined (parameters of physics and length of exposure), 90% to 100% of the animals exposed were cured. These animals then presented a phenomenon of therapeutic facilitation: some completely resistant to the re-administration of the pathogen which they had previously got rid of; others, to get rid of the re-administered pathogen, required a number of exposure sessions, but of significantly reduced length in comparison with the initial length which had enabled the first cure. The cured animals thus acquired a sometimes significantly increased state of immunity against the pathogen initially administered. These observations were confirmed by biological tests; in particular, the rates of antibodies specific to certain antigen structures of the pathogen reached considerable proportions. These effects were particularly confirmed when the animal was sufficiently mature, and its immune system was not seriously impaired by immunodepressors or X-rays.

The principal model which permitted these results at a biological level was Trypanosoma equiperdum, quite familiar to Professor R. PAUTRIZEL. But what in our eyes makes these effects even more significant, both on the therapeutic level and as far as the prospects for research that they open up go, is the fact that (a) the electromagnetic fields did not directly destroy the parasite and (b) this parasite, presenting the phenomenon of an antigen variation, always escaped the immune defenses of normal animals (those not treated) used for these experiments (mice, rats, rabbits).

In addition, the stimulation of immune defenses by these electromagnetic fields has been shown in other biological models (LS1, 347, Sal, T. gambiense, antibodies anti-peroxidase, in particular).

What is fundamental is that the cures by these electromagnetic fields had absolutely no side effects. The animals cured and the normal animals who were exposed were in perfect health and reproduced normally.

A hypocholesterolemiant effect was also noted [PAUTRIZEL, 1972/01].

Experiments with skin grafts (allografts and isografts) showed that these electromagnetic fields accentuate the ability of the organism to recognize "self" and "non self," as well as accelerate healing [CHATEAUREYNAUD, 1971, 1974].

In different circumstances and with a number of pathological models, a great deal of animal experiments were undertaken with different machines whose operation was assumed by A. PRIORE alone. These experiments were undertaken with the required rigour and reliability. The same experiments were repeated a number of times under the same conditions, always with unexposed controls, and always confirmed the same conclusive results. Thousands of mice and rats and numerous rabbits were used for this purpose. The biological and histological tests confirmed the clinical observations (observations of the external state of the animal).

Not only did these experiments meet the usual requirements, but given the controversy surrounding this research [GRAILLE, 1984], the researchers were obliged to submit to other types of requirements, which they did: verification experiment by R. COURRIER (Perpetual Secretary of the Academy of Science) in 1965; verification committee in 1969 with Bailif present and which included both university academics and non academics; University of Bordeaux II Thesis Committee in 1977.

For ethical reasons, A. PRIORE always sought the consent of the accepted medical spheres to start clinical explorations in humans. However, bowing to the disarray of patients and their families, backed up by their GP, and based on the undeniable results of his "Effect," he did finally conduct some very encouraging therapeutic investigations in patients with advanced stages of cancer. [DUBOURG, 1979].

The Principal Conclusions that we Have Drawn.

In general, the experiments show that the results obtained depend, amongst other things, on a certain number of parameters of physics. The biological results are of a different nature according to the type of illness or disease, the biological and/or clinical tests carried out: the time it took for parasites in the blood to disappear, the number of animals cured, the rate of antibodies, the speed of subsidence of tumours, and so forth. In what follows, we will assert that one physical configuration of parameters of physics presents greater biological effectiveness than a second configuration, with the same biological results obtained but with a total length of exposure lower than in the second configuration. We also mention therapeutic effectiveness in order to underline the fact that the biological effects can lead to cures.

In addition, in the case of a given disease or illness, the daily and total lengths of exposure to electromagnetic fields are determined according to the state of advancement of the illness or disease when therapy begins.

We define a parameter $\xi$, called biological effectiveness, which is purely formal in nature, since it represents the various quantifiable biological and clinical data.

Prior Instruments Used to Carry Out these Experiments, their Significance and their Limits.

The Technical State of the Prior Art in Question (Significance)

Two patents [PRIORE, 1963, 1966] describe the technicalities, often with details, constituting the two machines made by A. PRIORE. Later on, A. PRIORE built and supervised the construction of two other machines, i.e. a total of four machines.

On the technical level, all the machines are, in the main, based on a vertical, cylindrical, glass enclosure, containing a low pressure gas. This gas becomes ionized under the influence of various continuous and high frequency electromagnetic fields. The applicators of the high frequency fields were located in the upper part of the enclosure. At this level of the enclosure a cylinder, with paddles acting as anodes and which turned around the vertical axis of the enclosure, was to be found; an annular cathode heated by a filament was placed in the middle part of the enclosure. The high frequency fields of metric wave lengths were produced by high power generators (1 to several KW); a centimetric wave was produced by a magnetron.

The magnetic field coils were placed along the cylinder. The coil at the lower base of the enclosure was a voluminous element and required high capacity electric power to function.

The animals submitted to treatment were placed on a table under the enclosure, around its axis.

The Technical Problem Posed: Nature and Context (Limits).

As far as A. PRIORE was concerned, the overlap between instruments and biological experiments was essential: it was the biological experiments and their results that enabled him to break in and refine the parameters of his physics and it was the machines—through their successive transformations—which enabled him to optimize the therapeutic effects.

A. PRIORE died 1983 without having divulged the functioning of his machines to his collaborators. From that point, the problem became immediate: how to make the machines work, or how to reconstruct them in order to improve them, or how to build a new machine which would produce the same effects as PRIORE's machines. To this day, no publication, national or international, has offered any conclusive answers to these questions.

In the presence of PRIORE, a number of physicists undertook an analysis of the third machine that he had built and published their observations [BERTEAUD, 1971]. The authors indicate that at the level of the exposure table, they noted a magnetic field of 1 KGs with a pulsed wave of 9.4 GHz, and amplitude modulated at 17 MHz; the power of this wave, as a function of distance in relation to the axis, was between 0 and 700 µW (values obtained with a 64 cm$^2$ horn antenna). Unfortunately, this data did not permit the authors of the analysis to reproduce, with devices they themselves had made, the beneficial biological effects that were characteristic of PIORE's machines [GRAILLE, 1984].

Although the two patents that PRIORE did register enable one to begin to grasp his original process, the descriptions of the characteristics of the rays coming out of these machines are vague or even inaccurate: the term "complex rays" is used; electrically charged particles are said to be emitted in the direction of the subject to be treated, which in reality cannot be the case, in particular because of the walls of the enclosure. They do not mention either any potential procedures for adjusting the various devices which made up the machine, adjustments which only PRIORE himself knew.

It can be seen that, although the therapeutic effects of this "Effect" are divisible and can be shared, because they have been validated and confirmed, the "Effect" itself remains illusive. This strange paradox means that failing being able to walk in the visible footsteps of the discovery, it needs to be reinvented with new leads and down new tracks: in order to be able to decipher it better, to throw new light on it, to communicate it and thus optimise its full significance.

Our in-depth analysis of all this work in its entirety (publications, notes, manuscripts, etc.) has enabled us to grasp the characteristics which are specific to the rays of PRIORE's machine, rays which we believe are electromagnetic in nature. This new concept should enable new methods of technical construction which should be able to be developed industrially. These methods of construction, technically easier to implement, will be more energy-efficient. Thus the production of various types of instruments will be easier.

The Biophysicoclinical Process, Object of the Present Invention

Abbreviations: EM: electromagnetic; VHF: Very High Frequency; VE: volume of exposure.

Figure 1:
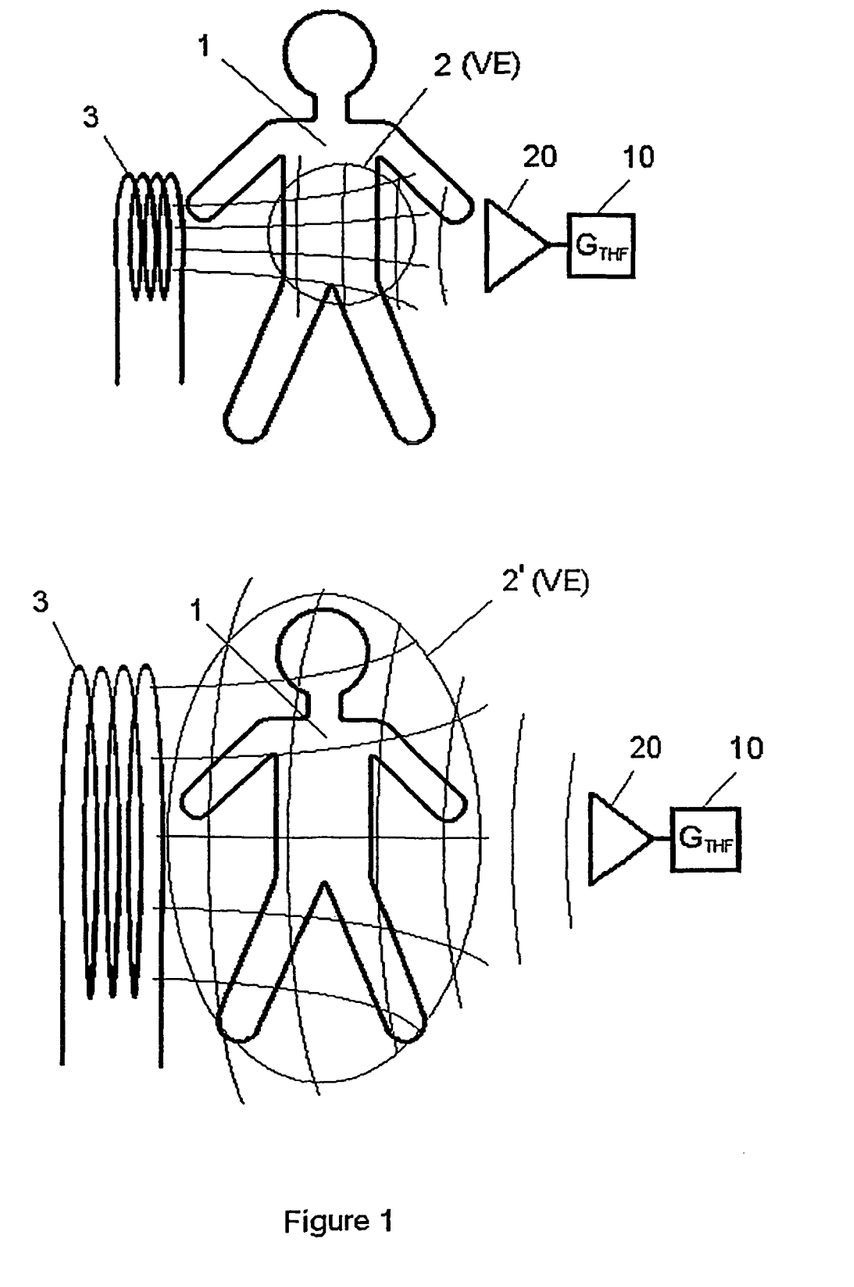
FIG. 1: Basic diagram respresenting process.

FIG. 1 gives a diagrammatic view of the process. The process consists in producing, using appropriate means (3), (10) and (20), and overlaying in the same volume, a magnetic field and one or several very high frequency {VHF} electromagnetic fields which have particular specifications. It is in this volume, called volume of exposure {VE}, that the subject to be treated (1) (animal or human being) is placed.

The VE (2) may be less than the total volume of the subject to be treated, in which case a part only of the subject is submitted to the simultaneous action of these fields. The VE (2') may be greater than the total volume of the subject to be treated, in which case the whole subject is entirely contained in the VE. The VE may be totally or partially delimited, or not, by material means. In addition to the physical specifications of the magnetic field and of the VHF EM fields, the biological and therapeutic effectiveness of this set of fields is all the greater if the VE is sufficiently large enough to contain all of the subject. On the other hand, a VE smaller than the volume of the subject means that the technical means implemented can be reduced and can be used in cases where a lesser biological effectiveness is sufficient, for example in pathological states which are more or less pronounced.

Continuing with the presentation, the physical parameters which characterize the process have values in certain ranges; these values must be chosen so as to optimize the biological or therapeutic effects, choices which depend on the biological model to be used or the illnesses and disorders to be treated.

The range of values announced are not exhaustive, but constitute typical values with which the effects can be obtained.

The magnetic field in the VE may be uniform in direction. For example, a magnetic field supplied by a magnet used in nuclear magnetic resonance imaging is suitable. In this case, the field is also of uniform intensity.

However, the magnetic field is not necessarily uniform, which significantly simplifies the technical implementation of the means used to produce said field. The direction of the magnetic field may vary in the VE according to some law of spatial coordinates or other; in this case, the intensity of the field will also vary since it obeys the principle of preserving the state of flux of the magnetic induction vector $B_0$:

$$divB_0=0$$

It should be remembered that in the air and in biological environments, the magnetic field vector $H_0$ and the magnetic induction vector $B_0$ are bound in very close approximation by the relation $B_0=\mu_0 H_0$, the constant $\mu_0$ being the magnetic permeability of the vacuum. However, to obtain good biological effectiveness, the configuration of the magnetic field in the VE should be preferably chosen so that the field is spread as wide as possible over the entire volume of the subject, and with a sufficiently high mean intensity in the volume of the subject. In other words, a higher intensity over the whole of the subject means that similar results can be obtained with shorter exposure times than with lower intensity and the field spread over only one part of the subject, and consequently a reduced VE.

The intensity of the magnetic field can be constant in time: the field is static.

The intensity of the magnetic field can also vary in terms of time. During this variation, the orientation of the field (i.e. the sense of a given direction) in any point of the VE can remain the same (unipolar) or be reversed (bipolar). The variation of the intensity in terms of time can be useful in the case where biological effectiveness turns out to not be simply proportionate to the intensity of the magnetique field, i.e. the differential in biological effectiveness in relation to the intensity of the field, $d\xi/dB_0$, is all the greater if the intensity is greater. Thus maximum intensity of the field can be increased in relation to a static field—at the level of the peaks of the function describing temporal variation—while maintaining power consumption identical to that required to create the static field with an electromagnet. The function describing temporal variation of intensity is preferably periodic, and its frequency spectrum is typically between 1 Hz and several tens of Hz.

Typically, the minimum value of mean intensity of magnetic induction in the VE—constant for a static field or peak in the case of variation—is in the region of 0.05 Tesla. As to maximum intensity, it is only limited by the technical means for implementation; values of 1 T or more may be necessary, in particular to overcome certain serious disorders or illnesses.

The magnetic field can be obtained in various ways:
one or several electromagnets consisting of electric conductor coils with suitable means of cooling;
a superconductor magnet consisting of a superconductor coil with associated cryogenic means;
one or several magnets consisting of blocks of materials presenting a permanent magnetic polarization, associated in a magnetic circuit if required, and this whatever the dimensions of the VE.

Figure 2:
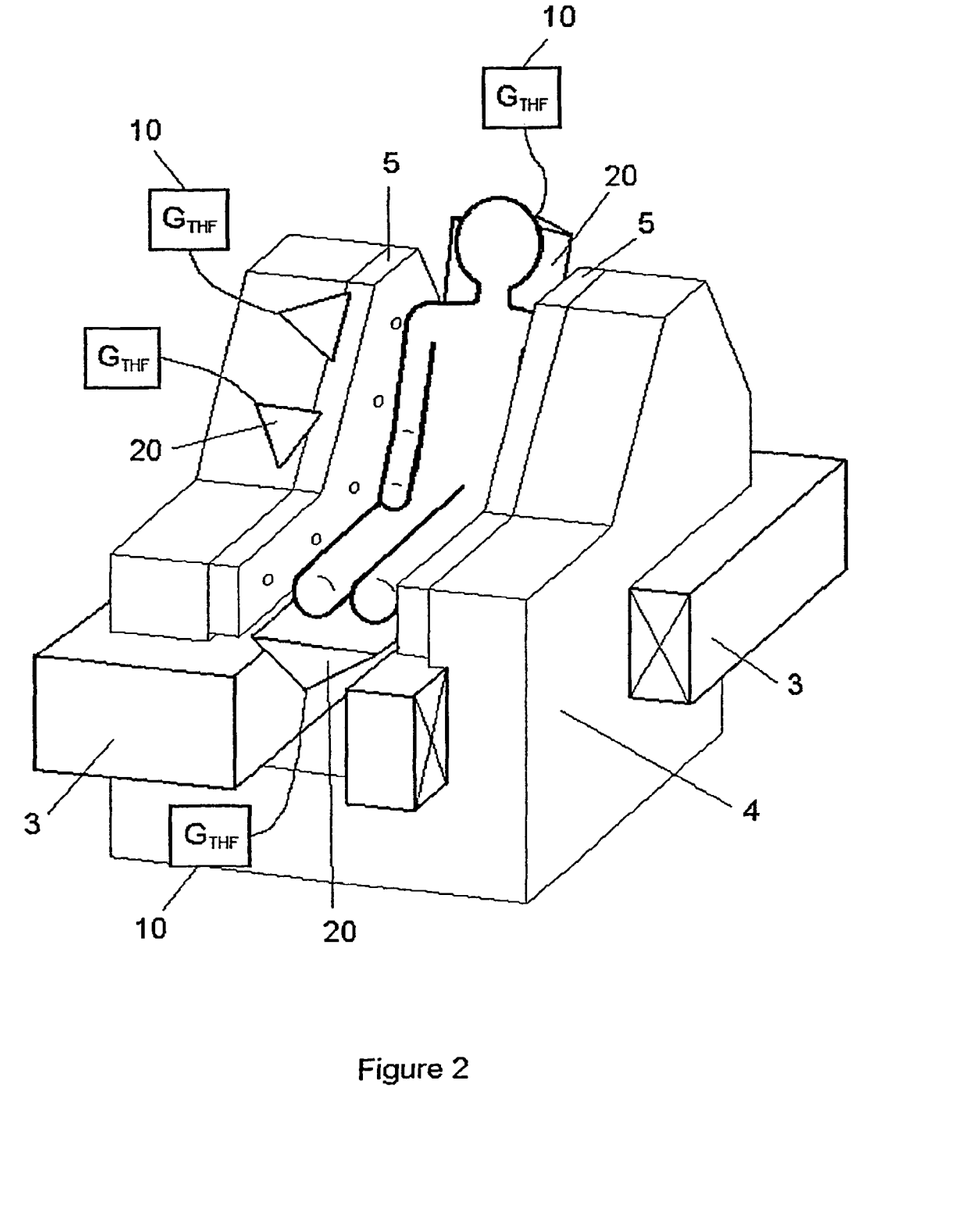
FIG. 2: Diagram representing one implementation of the process as a whole, open structure type.

FIG. 2 is a basic diagram showing one example of the process as a whole. It is supplied as an indication in the full knowledge that other forms and layouts of the constituent elements can be envisaged without limiting the significance of the invention.

If an electromagnet is used, the use of magnetic materials forming a magnetic circuit (4) will increase the intensity of the magnetic field by a given intensity of electric current in the coils (3), the VE being at the level of the gap between the two field poles (5); of course, to get the most out of the enlargement of the field, in relation to the field obtained with the same coils but without a magnetic circuit, the magnetic circuit must not be saturated.

Figure 6:
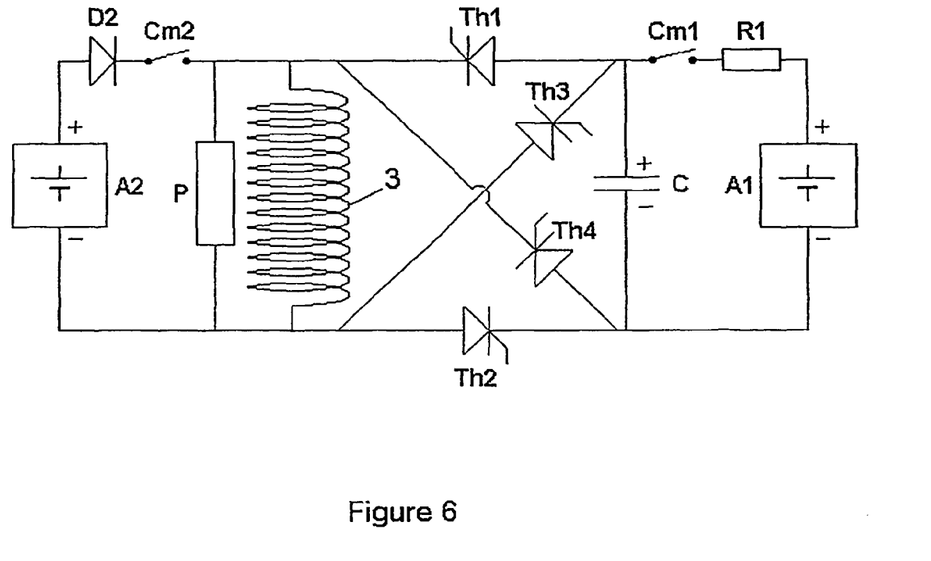
FIG. 6: Device enabling current variation in electromagnetic coil.

The principle of an electronic device to vary the intensity of electric current in the coil (3) of an electromagnet is indicated in FIG. 6. This device is organised around a bridge of four thyristors which means that the uptake times of the current in the coil are quicker than power switching (A2) alone (using the switch (Cm2)) and ensures that magnetic energy stored in the coil (3) is recovered in the capacitor (C) at each cycle; the magnetic field created is unipolar. This circuit means that polarized capacitors (e.g. electrochemical) can be used to advantage for (C), which usually have high capacity with limited congestion.

The timing diagram is as follows. To begin with all the thyristors are blocked and the switches open. Switch (Cm1) is closed and power supply (A1) charges the capacitor (C) through the resistance (R1). When the capacitor is charged to the desired voltage, the switch (Cm1) is opened. Switching pulses are then applied to the thyristor triggers (Th1) and (Th2) which renders them conductive and discharges the capacitor (C) into the coil (3); at the same time, the switch (Cm2) is closed, the function of the diode (D2) being to prevent a current in (A2) while the capacitor (C) is discharging. The rise in current in the coil practically follows a sinusoidal arc (apart from some loss due to conductivity). When the top of the sinusoidal arc is reached, the capacitor (C) being practically discharged, the thyristors (Th1) and (Th2) are blocked because of the voltage due to power supply (A2) which reverses the polarisation through diode (D2). The power supply (A2) takes up the relay by supplying current to the coil. The magnetic field is thus at its maximum and maintains a plateau at this rate for a certain time. Once this time has passed, the thyristors (Th3) and (Th4) are switched to an on-state by their switch trigger and the switch (Cm2) is open. The current stored in magnetic form in the coil (3) is then returned to the capacitor (C). The decrease in current here too practically follows a sinusoidal arc. When the current is cancelled out, the thyristors (Th3) and (Th4) are blocked. The switch (Cm1) is closed so as to supply the part of the electrical charge which has been dissipated by inductive heating in the ohm resistances of the circuit, in particular those of coil (3) in the case of a conductor, during this cycle. After a certain time, the process is repeated from the beginning. A crenellated, modulated magnetic field can thus be obtained, with an adjustable cycle ratio. The time of rise and descent t of a crenellation is shown in practice by the equation $t=\frac{1}{2}\pi\sqrt{LC}$, with L being the inductive reactance of the coil (3) and C the capacitive reactance of the capacitor (C). Voltage $V_C$ at which the capacitor (C) must be charged is given approximately by the equation $V_C=I_{max}\sqrt{L/C}$, where $I_{max}$ is the intensity of current to be reached to maintain the magnetic field in the plateau phase. The time of rise and descent is therefore consequently adjustable by choosing C, and $V_C$ is then adjusted; L is in fact fixed.

The electronic circuits not represented manage these stages of the cycle automatically and ensure that one pair of thyristors (Th1/Th2, Th3/Th4) is extinguished before another pair is opened (respectively Th3/Th4, Th1/Th2).

Safety elements can be placed on the coil (3) terminals—which in principal are very highly inductive—to avoid accidental overvoltage following a current circuit failure (A2) or that of a thyristor during the recovery phase (a spark gap with a swamping resistor, for example).

The frequency value that a VHF EM field will take corresponds to a wave length in the air in space which belongs to a decimeter or centimeter range. Therefore, for this range of values, and given the total volume of the subject to be treated, particularly where a human being is concerned, each VHF EM field is presented as an EM wave spread through the VE; this wave is emitted by an applicator acting as an antenna in the direction of the subject to be treated. The shape of the wave surface is not important: it can be flat or spherical, for example. The EM wave arriving on the subject exposed is called the incident wave and has several features which are the particularity of the present invention; it is this incident wave which, together with the magnetic field, produces the biological effects. At the interface between the subject and the medium of propagation, part of the incident wave penetrates the subject—the transmitted wave—while the other part is reflected; the transmitted wave fades as it spreads in because biological environments have complex permittivity which give rise to dielectric losses and losses through conductivity.

If several applicators are used, each applicator emits a VHF EM wave in the VE. We will indicate below the various parameters of one wave, it being understood that said parameters apply to all waves when several applicators are used. The values of the parameters may be identical for all waves, or differ, preferably in the range indicated, from one wave to another.

It should be remembered that the instant power $P_S$ of an EM wave through an open surface S is shown by the equation:

$$P_S = \int_S (E \times H) \cdot n \, dS$$

the integral bears on surface S, n being the normal vector at surface dS; $P_S$ is expressed in W/m²; E (in V/m) and H (in A/m) are respectively the vectors of the electric field and magnetic field of the wave. The scalar term $P=(E \times H) \cdot n$ therefore represents the instant power per surface unit or density of instant power of the wave. The density of average power between instants $t_1$ et $t_2$ is shown in the equation:

$$P_{moy} = (t_2 - t_1)^{-1} \int_{t_1}^{t_2} P \, dt$$

E and H are linked by the equation E/H=Z, where Z is the wave impedance. It should be noted that Z depends on the medium and the environment that the wave is propagated in: for example, impedance in unobstructed space in the air $Z_0$ is 377 ohms, whereas impedance at the exit or in the neighbourhood of an antenna (or other radiating element) is different from this value.

In order to describe the characteristics of an incident wave we shall start from a sinusoid EM signal—called a carrier signal—regardless of the structure in which it is propagated (guides, electronic circuits, neighbourhood of antenna, dielectric materials, unobstructed space), then we indicate the various operations which affect this carrier signal which will finally make up the incident wave applied to the subject to be treated. These operations are described mathematically and implemented using the appropriate technical devices. We define a quantity u to describe the temporal variations of this wave; t is the time variable. When, after the various operations affecting the carrier signal, u describes the incident wave, u refers indiscriminately to the module of electric field E, or magnetic field H in a given point, taken arbitrarily as origin of the phases.

First of all, the temporal variation of the carrier wave can be described by the equation:

$$u = A \cos(2\pi f_p t)$$

where A is the amplitude, and $f_p$ is the frequency of the carrier signal: it is situated typically between 1 GHz and 20 GHz. This frequency band, which is also that of the incident wave, is not limited but constitutes a good compromise between, on the one hand, a value necessarily sufficiently high to obtain the biological effects and, on the other hand, a sufficient depth of penetration to reach the biological tissue in which the effects are produced.

Despite this, for these frequencies, in the case of a relatively voluminous subject, such as a human being for example, and contrary to the magnetic field, the depth of penetration of the wave transmitted does not enable the deepest parts of the body to be exposed to the wave. Therefore, in order to optimize the biological and therapeutic effects, several applicators may be placed so as to surround the subject as much as possible: the incident waves will thus cover the entire surface of the subject as far as possible. For example, in the FIG. 2 diagram, the applicators (20) are placed over and under the subject. It is preferable to employ applicators here made from non magnetic materials (copper, conductive polymers, etc.) so as not to deviate and to concentrate the magnetic field lines on the applicators. Applicators can also be placed on both sides of the subject, coupled with the field poles (5) delimiting the magnetic head gap from the magnetic circuit; the applicators should preferably be flat so as to not enlarge the magnetic head gap. Applicators (20) placed under the subject may be covered with soft materials to ensure comfort; in this case, the incident wave is propagated in an environment presenting a wave impedance of unobstructed space equal to $Z_0/\sqrt{\in_r}$, where $\in_r$ is the relative dielectric constant of the materials chosen (having preferably little or no dielectric loss), relative permeability $\mu_r$ being supposed to be equal to the unit.

As for the magnetic field, the biological effectiveness of the process is an increasing function of the density of power of the incident wave. A possible non linear response of biological effectiveness in terms of the density of power of the incident wave (i.e. the derivative $d\xi/dP$ increases with P) may lead to modulating the amplitude of this wave. The time function of the wave is then expressed as:

$$u = AU(t)\cos(2\pi f_p t)$$

U(t) is the function of amplitude modulation and has terminals $|U(t)| \leq 1$. U(t) results indifferently from an amplitude modulation with or without carrier signal. In the case of an amplitude modulation with carrier signal, U(t) varies in terms of time between 1−m and 1, m being a positive constant between 0 and 1 and defines the modulation rate. A modulation rate equal to 1 should be chosen by preference (a modulation rate equal to 0 corresponds to the borderline case where the signal is not modulated). In the case of an amplitude modulation without carrier signal, U(t) is restricted to between −1 and +1 and the average value of U(t) is zero. Function U(t) is preferably periodic and its spectrum is typically between 1 Khz and 1 Mhz, apart from the line at 0 Hz in the case of a modulation with carrier signal. A good example consists in producing VHF wave trains with a high cyclical ratio; between each wave train, the amplitude is cancelled out. For example, with a frequency of 10 GHz, the duration of each wave train, which is almost rectangular in shape, is 1 µs, with a rise and descent time of ~0.25 µs, and the time between two successive wave trains is 1 ms; the cyclical ratio is therefore 1000, and the density of peak power of one wave train is 1000 times greater than the average power density. Other forms of wave trains can be envisaged: Gaussian, sinusoid arc, symmetrical or asymmetrical, for example. The relative phase between two successive wave trains can adopt any value, in particular when the cyclical ratios are high.

Whether it is amplitude modulated or not, the incident signal arriving on the subject does not necessarily produce an increase in temperature of body tissue. Indeed, one of the features of the process subject of the present invention is that the biological effects produced are not due to an increase in temperature of the whole or part of the subject exposed to these fields, as is sought after with certain physiotherapeutic methods, such as radio frequency diathermy or localized diathermy, in a limited part of the body by focalising microwaves on it with the object of destroying directly certain diseased tissue by heating (cancers in particular). Very good results, in particular in stimulation of the immune system, have been obtained with average power densities in the order of 10 µW/cm² in unobstructed space, and wave trains with a cyclical ratio of 1000; an average power density of this level cannot produce any appreciable heating of biological tissue. Average power density levels at which an appreciable increase in temperature is noted, either by instruments or by the patient himself, where human beings are concerned, should be considered as maximum levels which should not be exceeded.

Another essential feature of the process is that the incident wave presents an angle modulation: frequency modulation or phase modulation. Let us take the case of a frequency modulation which affects the carrier signal:

$$u = A \cos[2\pi(f_p + \Delta f(t))t]$$

$\Delta f(t)$ has a terminal function, proportional to the modulating signal $v_m(t)$:

$$\Delta f(t) = \alpha v_m(t)$$

$\alpha$ is a constant. This modulated frequency carrier signal can also be considered to be phase modulated:

$$u = A \cos[2\pi f_p t + \Delta \phi(t)]$$

with [FONTOLLIET, 1996]

$$\Delta \phi(t) = 2\alpha \int_0^t v_m(t) dt$$

In the case of a carrier signal with sinusoidal frequency modulation we have:

$$\Delta f(t) = \Delta f \cos(2\pi f_{m\delta} t)$$

the constant $\Delta f$ being the maximum frequency deviation on either side of the carrier signal; $f_{m\delta}$ is the frequency of the modulating signal. In this case, the equivalent phase modulation is also sinusoidal:

$$\Delta \phi(t) = \Delta \phi \sin(2\pi f_{m\delta} t)$$

$\Delta \phi$ is the maximum phase deviation. The modulation index is thus defined as $\delta$:

$$\delta = \Delta f / f_{m\delta} = \Delta \phi$$

The biological effectiveness $\xi$ of the process is a function of the modulation index. When $\delta$ is nil, the biological effectiveness of the process is nil or almost nil. Typically, the minimum value of $\delta$ which enables tangible biological effects to be obtained is in the order of $\pi/4$.

It is preferable that the frequency of angle modulation be situated between 10 and 300 MHz. This frequency band is not restrictive but enables, (a) to rapidly modulate the carrier wave frequency and, (b) to technically reach modulation indices sufficiently high in relation to the band frequency chosen for the carrier signal; these two conditions—sufficiently high modulation frequency and modulation index—are necessary to obtain biological effects. For example, with $f_{m\delta}$=50 MHz et $\delta = \pi/2$, we obtain $\Delta f \approx 78$ MHz; this deviation of frequency should be compared with the carrier signal frequency ($f_p$=10 GHz, for example).

Other forms of modulation signal can be chosen according to the biological effectiveness they permit. They should preferably be periodic with a frequency spectrum typically between 10 and 300 MHz.

A further feature of the process of the present invention is that the incident wave undergoes a continual change in state of polarization in terms of time. All along the interface between propagating medium/exposed subject, a given state of polarization of the incident signal gives way in time, either continuous or in skips, to another state of polarization. Biological effectiveness is improved in comparison with a fixed, rectilinear polarization, when the state of polarization undergoes these variations.

We can define in general terms the state of polarization of a wave if we consider that it is the result of the superimposition, mathematical or physical, of two waves of the same frequency which have their wave vectors merged, each with the following rectilear polarization, respectively, axes X and Y need to be perpendicular to each other [BORN, 1964]; at a given point, the magnetic field component—arbitrarily E or H—of each wave has the value (complex notation):

$$u_x = p_x \cdot u$$

$$u_y = p_y \cdot e^{j\theta} \cdot u$$

$p_x$ et $p_y$ are the amplitudes of the two waves and have real values; $\theta$ is the phase shift between the two waves; u represents, as before, the carrier signal modulated in amplitude and in angle, and it is expressed here implicitly in complex form. For a resulting wave spreading in unobstructed space, the vector wave is perpendicular to the XY plane. Thus, according to values $p_x$, $p_y$ and $\theta$, we obtain different states of polarization. By varying these parameters in terms of time, the state of polarization varies; for this reason we call $p_x(t)$, $p_y(t)$ and $\theta(t)$, functions of modulation of polarization. In what follows, we shall consider that:

$$p_x^2(t) + p_y^2(t) = \text{constant}$$

for if this is not the case, the resulting wave is affected in amplitude by $p_x(t)$, $p_y(t)$; in practice, amplitude modulation is achieved by a device expressly for this purpose. We use the constant equal to 1 to signify that the VHF EM energy is not reduced—or practically not—by the device which creates the variation in state of polarization.

Different variations in the state of polarization can be envisaged as part of the present invention.

For example, for $\theta$=constant=0, the resulting polarization is rectilinear. The angle of polarization $\psi$, between axis X and the direction of polarization, is given by the time function:

$$\psi(t) = 2 \arctan[p_y(t)/(p_x(t)+1)]$$

since $p_x^2(t) + p_y^2(t) = 1$; $\psi$ can vary in continuous fashion, or take discrete values, depending on a periodic or random evolution. For $\psi(t)$ it is preferable to choose a function with a uniform or almost uniform probability density extending between $-\pi$ et $\pi$ (or 0 and $\pi$). Thus, typically, we take:

$$p_x(t) = \cos 2\pi f_{mp} t$$

$$p_y(t) = \sin 2\pi f_{mp} t$$

for a continuous and periodic variation of $\psi$; $f_{mp}$ is the modulation frequency of the state of polarization and is typically between 1 Hz et 100 Hz.

If we opt for discrete states of polarization, the modulation functions of polarization are discrete. For example, let us take the case where θ=0 and take successively for $\{p_x, p_y\}$, for identical durations, the following discrete value pairs forming a cycle: $\{1,0\}$, $\{1/\sqrt{2},1/\sqrt{2}\}$, $\{0,1\}$, $\{-1/\sqrt{2},1/\sqrt{2}\}$, $\{-1,0\}$, $\{-1/\sqrt{2},1/\sqrt{2}\}$, $\{0,1\}$, $\{1/\sqrt{2},1/\sqrt{2}\}$, $\{1,0\}$. Thus, during a cycle, ψ varies between 0 and π by taking the discrete values separated by 45°; ψ(t) has a uniform probability density. The duration of a cycle is typically between 0.01 s and 1 s.

Another example of modulation of the state of polarization consists in taking θ=constant=±π/2 and make $p_x(t)$ and $p_y(t)$ vary at frequency $f_{mp}$. Thus, at the instants where $|p_x(t)|=1$ and at the instants where $|p_y(t)|=1$, polarization is rectilinear following respectively axis X and axis Y. When $|p_x(t)|=|p_y(t)|=1/\sqrt{2}$, polarization is circular and turns in one direction or the other—right or left—following the sign of ratio $p_y(t)/p_x(t)$. For the other values of $p_x(t)$ et $p_y(t)$, polarization is elliptical, right or left, and the two principal axes of the ellipse remain merged respectively with X and Y. In this case, ψ is therefore always nil.

This variation in the state of polarization can also be obtained by maintaining $p_x=p_y=1/\sqrt{2}$ fixed, and varying θ between −π et +π, with the difference that ψ remains equal to ±π/4; the sign ψ depends on the principle axis chosen as axis of polarization.

Other variants of the variation of state polarization can be envisaged as, for example, varying the direction of the long axis of an elliptical polarization where the elliptical ratio remains constant, with a fixed direction, while still remaining within the present process.

Figure 7:
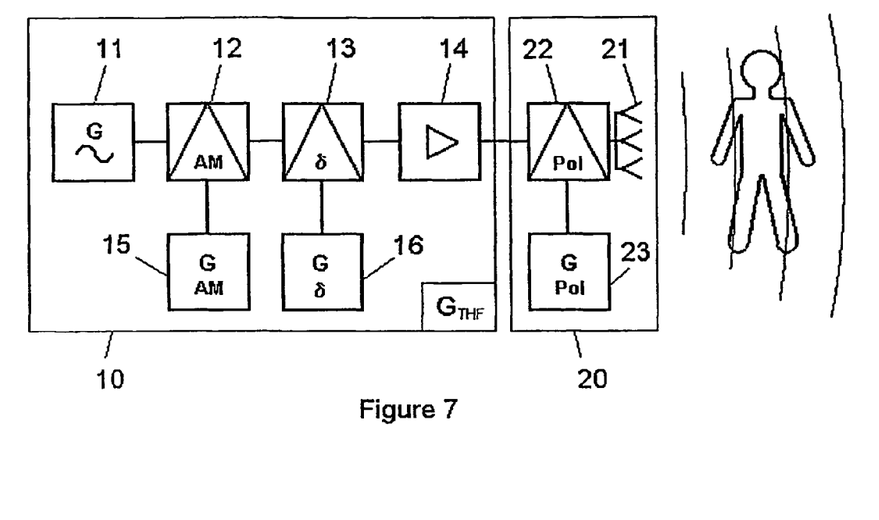
FIG. 7: Wiring diagram of device enabling production of VHF EM field.
Figure 8:
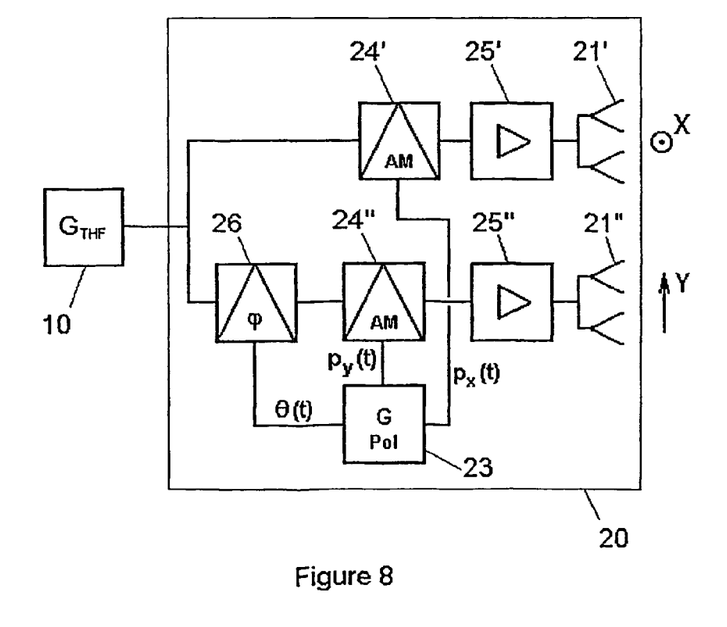
FIG. 8: Wiring diagram of device, sub system of device in FIG. 7, enabling polarization variation of VHF EM field.

The increase in biological effectiveness due to variation in the state of polarization, in relation to a case of fixed rectilinear polarization, may arise from the fact that, at the biochemical level, the molecules causing the biological effects are oriented in random fashion in the body and that each molecule, in order to be more effectively triggered, requires that the direction of polarization in particular, be close to an optimum value. Thus a greater number of molecules are, statistically, triggered. In addition, variation in the state of polarization enables the interference nodes caused by the various reflections which the incident wave undergoes to be displaced; the subject is thus exposed uniformly—on average during the time—to the incident wave over the entire surface contained in the VE.

In FIG. 7 we provide, in the form of building blocks, the wiring diagram of a device enabling production of the VHF EM incident wave, object of the process of the present invention. An oscillator (11), producing a sinusoidal signal at a given frequency for the carrier signal, is followed by an amplitude modulator (12), which itself is followed by an angle modulator—phase or frequency—(13). The signal modulated in amplitude and in angle which results is eventually amplified by an amplifier (14) in order to obtain the density of power desired at the level of the subject to be treated. The components at the exit of the modulators—in particular the amplifier (14), when it is used, and the applicator (20)—must be chosen so as to let the spectral components which result from the modulations pass. The spectral components resulting from the angle modulation spread in theory through an infinite width around the frequency of the carrier signal, but we limit this width, as is done in radio broadcasting, to a bandwidth containing ~98% of the power of the incident wave which would be obtained if the bandwidth were of an infinite width.

In general, electronic assemblies to make building blocks can use either semi-conductor components (transistors, diodes Varicap, PIN, etc. . . . ) or electronic tubes (travelling wave tubes {TWT}, magnetrons, klystrons, etc.).

In addition, the various functional blocks in FIG. 7 can be laid out differently depending on the technical means chosen. We are giving below a few variations, for information only, whilst adding that this information can in no way limit the significance of the present invention. In the case of an amplitude modulation in the form of virtually rectangular wave trains, a magnetron oscillator can be used with a power voltage proportionate to the modulation signal, followed by a second magnetron mounted with reactive impedance to execute the angle modulation; the power of the oscillator magnetron will then be sufficient and an amplifier is not necessary. Or again, a TWT amplifier may be controlled by the amplitude modulator signal by means of a grid controlling the electronic beam: the amplitude modulator is thus merged with the amplifier, the carrier signal being angle modulated before being injected into the VHF entrance of the TWT. Or again, the angle modulator and the VHF oscillator may be merged: reactive element acting on the resonant frequency of a cavity in which an oscillator element is placed; or a magnetron with crossed beams.

The variation in the state of polarization is insured by the applicator (20). The applicator consists, in general, of a polarization modulator (22), controlled by one or several modulation signals produced by the generator (23), followed by one or several radiating elements (21). The polarization modulator may be situated in proximity to the radiating elements, integrated into their mechanical structure, or sited in a separate device.

A simple example of the implementation of such a device consists in using a horn antenna in rectangular guide that is turned around its emission axis at a constant angular speed. The passage through the horn of the modulated VHF EM signal produced by the generator (10), is effected using a rotating rod transition: the resulting polarization is rectilinear and its direction turns around the wave propagation axis; we have −π≤ψ≤π, and ψ(t) is a function with a uniform probability density.

An other example of implementation is to use two helicoidal antenna, coiled respectively clockwise and anticlockwise, into which are injected by turns with the assistance of a switching device, VHF EM excitation; the result is the emission of a VHF EM wave which alternately presents polarization to the right and to the left, i.e. two states of discrete polarization.

A network type antenna can also be implemented having several radiating elements such as represented in the wiring diagram in FIG. 8. The network is divided into two sub-networks of radiating elements: the elements of the first sub-network (21') emit a rectilinear polarized wave along axis X, the elements of the second sub-network (21") emit a rectilinear polarised wave along axis Y, X and Y being orthogonal; these two waves have their wave vectors merged or practically merged. The radiating elements can, for example, consist of slits made in the wave guides, slits all on a plane parallel to the XY plane. Into each of the two sub-networks, a VHF EM wave produced by the generator (10) is injected and then respectively modulated in amplitude by an amplitude modulator (24') (24"); each amplitude modulator is controlled respectively by a polarization modulation signal $p_x(t)$ and $p_y(t)$, produced by the generator (23); the two waves are phase shifted between each other by the phase modulator or phase shifter (26), which phase modulator or shifter is controlled by the polarization modulation signal θ(t).

In addition to electromechanical means of modulation, elements based on semiconductors can also be used in the modulators such as, for example, PIN diodes for amplitude modulators (24')(24") and Varicap diodes for the phase shifter (26). In this case, it would be well advised to place an amplifier, respectively (25') and (25"), in each of the injection routes in the sub-networks, for these semi-conductors have limited admissible power; thus the modulated VHF generator (10) will have at the most a low power amplifier (14). In the case of modulation with discrete polarization, these semi-conductors are controlled by signals taking discrete values.

In the case of the use of several applicators each emitting a VHF EM wave, a single generator (10) need be used; the amplitude, angle modulated, and if required amplified, carrier signal, is distributed more or less identically between each applicator, or directed towards each applicator one after the other in whatever order using VHF switches. Or, each applicator is excited by a dedicated generator (10); the advantage of this second layout is that each generator taken individually provides appreciably less power compared to the implementation of a single generator for several applicators.

Prospects which the Present Invention Opens Up: at the Level of Applications (Somatic and Psychosomatic) and at the Research Level.

1—Therapeutic: infectious diseases, cancers, vascular illnesses, regeneration of injured tissue and in general illnesses where the effects on the immune system would be beneficial. Tissue regeneration in particular, in the case of burnt skin tissue: autografts carried out on the injured part of the subject, said subject then being exposed to the process, object of the present invention and which has the effect of accelerating adherence, development and healing of grafted tissue.

2—Preventive: activates the immune system even if there is no pathogen, antigenic; the immune system thus becomes better equipped to react against a pathogen appearing later on. Acts as an immunostimulant during vaccination without producing the side effects of certain chemical immunostimulants.

3—Diagnostic: enables, for example, determination of the state of immune response to an antigen test.

4—Biotechnological: use of the process, object of the present invention, within a process susceptible to industrial application whereby a biological substance is obtained, in particular, immunoserums, polyclonal antibodies with a defined specificity, or monoclonal antibodies reacting specifically with a given antigen (molecule, infectious agent, attenuated microorganism, cell, etc.).

To do this, a given antigen is administered to a live subject; this subject is exposed to the magnetic and electromagnetic fields to stimulate immune defenses which then produce antibodies; liquids are taken from the subject with which an immunoserum is obtained by filtering; specific antibodies reacting specifically with the administered antigen are obtained after purification of said immunoserum.

Monoclonal antibodies are obtained in the following manner: a given antigen is administered to a living subject; this subject is exposed to the magnetic and electromagnetic fields to stimulate immune defenses which will then contain the lymphocytes which produce antibodies; tissue samples containing lymphocytes which produce antibodies is then taken from the subject; monoclonal antibodies can be produced from the lymphocyte cells of this tissue. A cloning technique such as that of hybridomes can be used here [Roitt, 1989]: this technique consists of putting into suspension cells from tissue samples taken, to fuse these cells with the cells of the myeloma and then to select and clone the hybrid cells thus obtained which are producers of antibodies, said antibodies having the specificity required vis-a-vis the antigen.

The antigen may be naturally present in the body and it is not therefore necessary to administer it to the living subject. In particular, it may be an antigen related to a cancer activity in the body. Thus with one of these two processes, where the phase of administration of the antigen is not implemented, antibodies specific to this antigen can be obtained.

The advantage of the two above-mentioned processes, in relation to the usual processes whereby a biological substance is obtained, but which do not use the process, object of the present invention, is that they enable a more rapid immune response which is quantitatively higher, both in antibodies and in lymphocytes producing specific antibodies and with better antigen specificity, i.e. with a higher affinity constant of the reaction antigen-antibody. These two processes for obtaining biological substances are particularly interesting in cases where the antigen presents a low immunogenicity.

Monoclonal antibodies, conditioned alone (derived from a single clone) or combined between them, can constitute tools for tests and immunological analyses and be used for therapeutic purposes.

In general, there are places to treat mental disorders and places to treat illnesses and disorders of the body. Today, what is important is to develop links between the different approaches and to look at a patient as a whole.

This is exactly what the process, object of the present invention tries to do; to permit clinical practice which can correlatively stir the various fragments—mental and physical, mind and body—to move towards a global approach. With a global approach the patient can feel that our desire is to bring him peace.

The therapeutic effects inherent to this process equate to a vital and revitalising energy which will enable the patient to recreate—in time—his own vitality. He can see the energy coming from the outside give way to the energy coming from inside. If this particular transfer of energy at a different level is possible, it is because the rays work like a catalyser, but do not alter the psychosomatic and somatic integrity of the patient, has no harmful side effects and does not create a dependence on any substance.

Examples of Attainments of the Biophysicoclinical Process.

The structure and the layout of the various elements comprising the instruments comply with clinical requirements.

For instance, patients who are also claustrophobic would have difficulty finding themselves inside a cylinder consisting of a magnet from a nuclear magnetic resonance imager. In addition, as far as the process object of the present invention is concerned, exposure times can sometimes be relatively long (several hours a day). The design of the structure therefore needed to be open where the shape of the gap of the magnetic circuit enables the subject to be seated or lying down, and where the greater part of the volume of a subject can be exposed to the magnetic field. This instrument is a prototype of an open structure. (FIG. 2).

Figure 3:
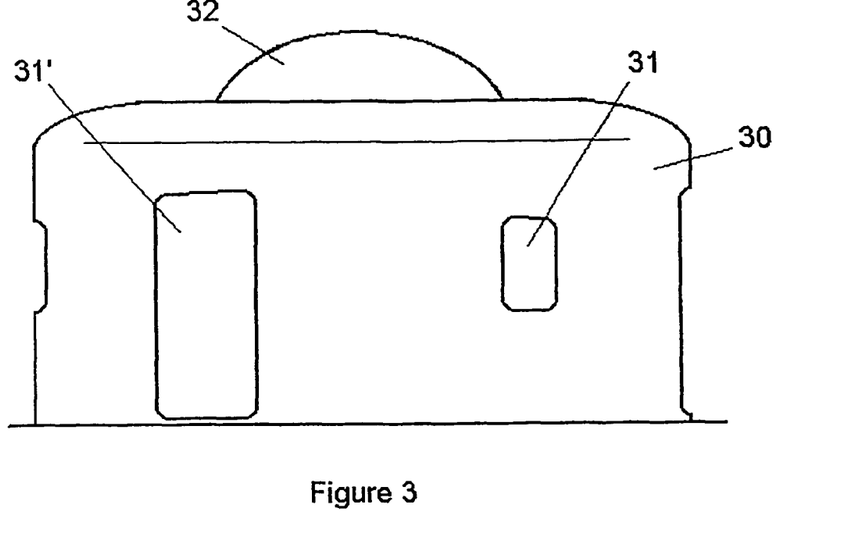
FIG. 3: Diagram representing exterior view of one implementation of the process as a whole, closed type structure.
Figure 4:
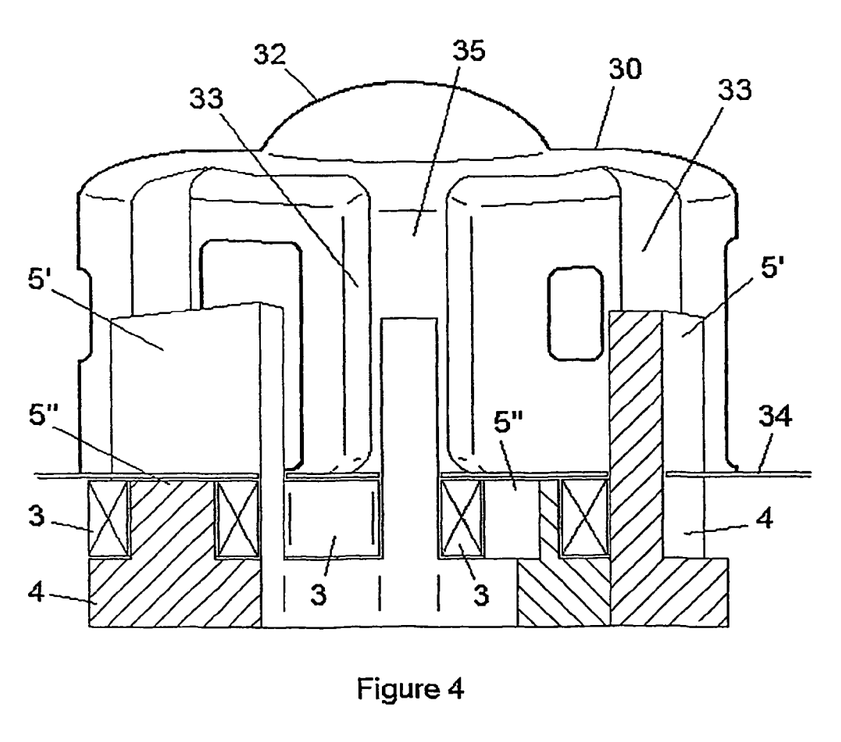
FIG. 4: Diagram representing interior view in vertical section of closed structure; profile drawings are indicated in FIG. 5 (broken line AA').
Figure 5:
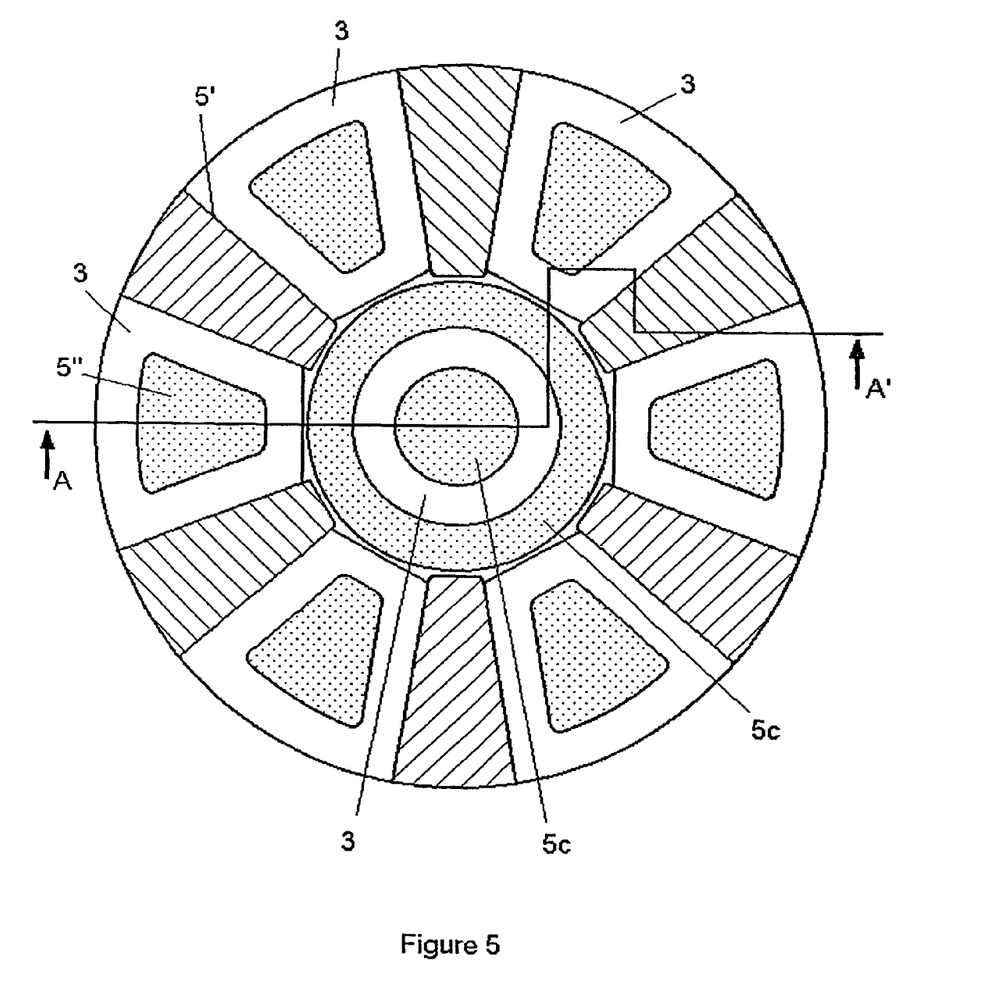
FIG. 5: Basic diagram representing interior view in horizontal section of closed structure showing layout of parts constituting the magnetic circuits.

The other prototype is that of a closed structure (FIGS. 3, 4, 5). Well adapted for small children, in particular autistic children taken in holistic, psychosomatic globality. It should neither close them in, nor prevent them from moving, nor remove them from the presence of the adults in their world (health professionals, family). Having a need for a receptacle-envelope which puts them together from the inside, inside, and protects them from the outside. In other words a container which, made reliable and safe in spoken terms, becomes a source for tentative containing identification enabling the child to draw unifying perceptions of himself.

FIG. 3 shows an exterior view of this structure. FIG. 4 shows an interior view of the structure in vertical section, the basic diagrams of which are indicated in FIG. 5 by he broken line AA'. FIG. 5 shows a view of the elements making up the magnetic circuit from above and in horizontal section formed by the floor (34).

Seen from the outside, this structure is circular in shape (30), on a vertical axis, with a diameter in the region of 2.5 m, surmounted by a translucent dome (32); the dome means that the inside of the structure can be lit by lighting placed above. Inside it consists of a central circular space of about 1 meter in diameter, situated below the dome (32), surrounded by lateral wings, numbering six, for example, each separated by vertical, radial partitions (33). Each lateral wing may have one opening (31) or one passageway (31') communicating with the outside. In general, the shape of the structure, both inside and out, is round and has no angular parts. Between two partitions (33) separating two adjacent wings a field pole (5') is placed; associated with the field pole (5') of one or other wing, at floor level (34), they form a gap; the magnetising coils (3) or the magnetic materials (according to the technical solution opted for) and the remainder of the magnetic circuit (4) are placed under the floor (34). In FIG. 4, the circular magnetic circuit enabling a magnetic field to be placed in the central space is not shown; this magnetic circuit is shown in FIG. 5 where the field poles (5c) can be seen, at floor level, and the associated coil (3). In the case where electromagnets are used, the coil producing the magnetic field in the corresponding wing is supplied with electric current only if a child is present in the wing; monitoring is automatic, using presence sensing devices.

The applicators (not shown) of the VHF EM fields are hidden behind the partitions (33), in the volumes (35), for example. The structure is preferably made from composite materials such as fibreglass impregnated with polymerised resin; these materials have no magnetic properties (relative permeability very close or equal to à l'unité), present a relative permittivity in the region of 2 to 3 permitting the passage of VHF EM fields emitted by the applicators, and are resistant and have a cushioning effect in case a child should fall.

These two prototype structures, open and closed, are each part of a pacifying global mediation approach concerning the patient as a whole.

Looked at from the clinical point of view—infantile autism, in particular—a structure is both receptacle and envelope. Receptacle destined to receive, to contain and to channel the invisible energy (the electromagnetic fields); a protective envelope made dependable and safe in verbal terms.

The shape and the layout of the elements which make up these structures for use with human beings are fixed by clinical practice:
  subject to be treated: child, adult, whole body or part of body;
  context of use: static, play aspect;
  fields of application: diagnostic, preventive, therapeutic;
  specificity of illness and diseases to be treated: principally somatic (cancer, infections, allergies, etc.), or principally psychic trauma (autism, psychoses, etc.);
  different approaches of different practitioners: use of the structure by psychotherapists, doctors or a global health professional;
  types of indications: use of the receptacle/envelope structure alone, or its integration into a global project: the receptacelenvelope structure can be used alone without diagnostic and/or preventive designs. However, it must be associated with other types of mediation for therapeutic reasons (the paddling pool, for instance, for autistic infants).

BIBLIOGRAPHY

BORN, M. and WOLF, E. (1964). *Principles of Optics*. Pergamon Press, second edition, 1964.
FONTOLLIET, P. G. (1996). *Systèmes de télécommunications*. Traité d'Electricité, volume XVIII, Presses polytechniques et universitaires romandes, Lausanne, 1996.
ROITT, I. & BROSTOFF, J. & MALE, D. (1989). *Immunologie fondamentale et appliquée*. Medsi/McGraw-Hill, 2$^{ème}$ edition, Paris, 1989.

BIBLIOGRAPHY CONCERNED WITH PRIORE EFFECT

BERTEAUD, A. J. & BOTTREAU, A. & PRIORE, A. & PAUTRIZEL, A. N. & BERLUREAU, F. et PAUTRIZEL, R. (1971). *Essai de corrélation entre l'évolution d'une affection par Trypanosoma equiperdum et l'action d'une onde électromagnétique pulsée et modulée*. Comptes rendus de l'académie des sciences (Paris), n° 272, p. 1003-1006, série D, 15 février 1971.
CHATEAUREYNAUD-DUPRAT, P. (1971). *Rapport d'activitédu 1$^{er}$ mars 1970 au 1$^{er}$ mars 1971*. Compte rendu au CNRS, 25 février 1971.
CHATEAUREYNAUD-DUPRAT, P. (1974). *Effets des ondes EM et des champs magnétiques modulés sur les phénomènes de defense de l'organisme*. Extraits des titres et travaux scientifiques, CNRS, 1$^{er}$ septembre 1974.
DELMON, G. et BIRABEN, J. (1966). *La croissance du carcinome de Guérin sous l'action de champs magnétiques*. Revue de pathologie comparée, T3-2-775, p. 85-88, Février 1966.
DUBOURG, G. & COURTY, G. & PRIORE, A. et PAUTRIZEL, R. (1979). *Stimulation des défenses de l'organisme par association d'un rayonnement électromagnétique pulsé et d'un champ magnétique: tentative d'application au traitement du cancer chez l'Homme*. Symposium international des thérapeutiques ondulatoires, Versailles, 19-20 mai 1979. Proceedings of International Symposium on Wave Therapeutics ISBN 2-904414-00-2, p. 198-208.
GRAILLE, J. M. (1984). *Le dossier PRIORE. Un nouvelle affaire PASTEUR?*. Edition Denoël 1984.
GUÉRIN, M. et GUÉRIN, P. (1934). *Epithélioma de l'uterus du rat, lymphotrope et transplantable*. Bulletin de l'association française pour l'étude du cancer, vol. 23, p. 632, 1934.
MAYER, G. & PRIORE, A. & MAYER, G. et PAUTRIZEL, R. (1972). *Action de champs magnétiques associés à des ondes électromagnétiques sur l'orchite trypanosomienne du Lapin*. Comptes rendus de l'académie des sciences (Paris), tome 274, série D, p. 3011-3014, 29 mai 1972.
PAUTRIZEL, R. & RIVIÈRE, M. R. & PRIORE, A. et BERLUREAU, F. (1966). *Influence d'ondes électromagnétiques et de champs magnétiques associés sur l'immunité de la souris infestée par Trypanosoma equiperdum*. Comptes rendus de l'académie des sciences (Paris), tome 263, série D, p. 579-582, 1$^{er}$ août 1966.
PAUTRIZEL, R. & PRIORE, A. & BERLUREAU, F. et M$^{lle}$ PAUTRIZEL, A. N. (1969). *Stimulation, par des moyens physiques, des défenses de la souris et du rat contre la Trypanosomose expérimentale*. Comptes rendus de l'académie des sciences (Paris), tome 268, série D, p. 1889-1892, 9 avril 1969.
PAUTRIZEL, R. & PRIORE, A. & BERLUREAU, F. et M$^{lle}$ PAUTRIZEL, A. N. (1970). *Action de champs magnétiques combinés a des ondes électromagnétiques sur la trypanosomose*

*expérimentale du lapin*. Comptes rendus de l'académie des sciences (Paris), tome 271, série D, p. 877-880, 7 septembre 1970.

PAUTRIZEL, R. & MATTERN, P. & PRIORE, A. & M$^{lle}$ PAUTRIZEL, A. N. et BERNARD, D. (1971/09). *Etat de protection vis-à-vis de Trypanosoma equiperdum chez des souris splénectomisées et soumises à une stimulation physique*. Comptes rendus du 1$^{er}$ Multicolloque européen de parasitologie à Rennes, p. 116-118, 1$^{er}$ au 4 septembre 1971.

PAUTRIZEL, R. & PRIORE, A. & DALLOCHIO, M. et CROCKET, R. (1972/01). *Action d'ondes électromagnétiques et de champs magnétiques sur les modifications lipidiques provoquées chez le lapin par l'administration d'un régime alimentaire hypercholestérolé*. Comptes rendus de l'académie des sciences (Paris), tome 274, série D, p. 488-491, 17 janvier 1972.

PAUTRIZEL, R. et PRIORE, A. (1974). *Effects of Priore apparatus in some different models*. Présenté à la Réunion sur les effets biologiques des radiations électromagnétiques non ionisantes à New York, février 1974.

PAUTRIZEL, R. & PRIORE, A. & MATTERN, P. & M$^{lle}$ PAUTRIZEL, A. N. et CAPBERN, A. (1975). *Guérison de la trypanosomiase chronique du lapin à Trypanosoma equiperdum par l'action combinée de champs magnétiques et d'ondes électromagnétiques*. Journal de Protozoologie, tome 22, n° 3, A84, 1975.

PAUTRIZEL, R. & PRIORE, A. & MATTERN, P. et M$^{lle}$ PAUTRIZEL, A. N. (1975/04). *Stimulation des défenses de la souris trypanosomée par l'action d'un rayonnement associant champ magnétique et ondes électromagnétiques*. Comptes rendus de l'académie des sciences (Paris), tome 280, série D, p. 1915-1918, 28 avril 1975.

PAUTRIZEL, R. (1976). *La trypanosomiase expérimentale: stimulation des défenses de l'organisme par des moyens physiques*. XVIIth Seminar on Trypanosomiasis Research, London, 23-24 septembre 1976.

PAUTRIZEL, R. & MATTERN, P. & M$^{lle}$ PAUTRIZEL, A. N. et PRIORE, A. (1977). *Effets des champs magnétiques et des ondes électromagnétiques modules sur la trypanosomiase expérimentale*. Annales de la société Belge de médecine tropicale, tome 57, n° 4-5, p. 501-523, 1977.

PAUTRIZEL, R. & MATTERN, P & PRIORE, A. & M PAUTRIZEL, A. N. & CAPBERN, A. et BALTZ, T. (1978/05). *Importance des mécanismes immunitaires dans la guérison de la trypanosomiase expérimentale par stimulation physique*. Comptes rendus de l'académie des sciences (Paris), tome 286, série D, p. 1487-1492, 22 mai 1978.

PAUTRIZEL, R. & PRIORE, A. & M$^{lle}$ PAUTRIZEL, A. N. et M$^{me}$ CHATEAUREYNAUD-DUPRAT, P. (1978/09). *Influence de l'âge de la Souris sur l'efficacité de la stimulation de ses défenses par un rayonnement électromagnétique*. Comptes rendus de l'académie des sciences (Paris), tome 287, série D, p. 575-578, 18 septembre 1978.

PAUTRIZEL, R. et PRIORE, A. (1979/04). *Un aspect spectaculaire du bioélectromagnétisme: permettre à l'organisme hôte de se débarrasser d'une infection aiguë ou chronique sans l'aide d'aucune substance médicamenteuse*. Communication présentée au 104$^e$ congrès national des sociétés savantes (Bordeaux), section sciences, p. 112, 17-21 avril 1979.

PAUTRIZEL, R. et PRIORE, A. (1979/05/a). *Guérison de la trypanosomiase expérimentale par association de champs magnétiques et d'ondes électromagnétiques*. Symposium international des thérapeutiques ondulatoires (Versailles), p. 9, 19-20 mai 1979.

PAUTRIZEL, R. & M$^{me}$ CHATEAUREYNAUD-DUPRAT, P. & PRIORE, A. et M$^{lle}$ PAUTRIZEL, A. N. (1979/05/b). *Guérison d'une trypanosomiase mortelle*(T. equiperdum injectée aux souris) par des moyens physiques. Symposium international des thérapeutiques ondulatoires, Versailles, 19-20 mai 1979. Proceedings of International Symposium on Wave Therapeutics ISBN 2-904414-00-2, p. 193-197.

PAUTRIZEL, R. & PRIORE, A. & M$^{lle}$ PAUTRIZEL, A. N. et M$^{me}$ CHATEAUREYNAUD-DUPRAT, P. (1979/06). *Guérison d'une trypanosomiase expérimentale par l'association de champs magnétiques et d'ondes électromagnétiques: une stimulation des défenses de l'organisme*. Communication présentée aux Journées nationales micro-ondes, Colloque optique hertzienne et diélectrique (Lille), p. 31, 26-29 juin 1979.

PAUTRIZEL, R. (1979/11). *Utilisation des champs magnétiques et des ondes électromagnétiques*. Communication présentée au 2$^e$ Symposium international des médecines bioénergétiques (Paris), 25 novembre 1979.

PAUTRIZEL, R. & PRIORE, A. & M$^{me}$ CHATEAUREYNAUD-DUPRAT, P. et M$^{lle}$ PAUTRIZEL, A. N. (1981). *Immunostimulation by electromagnetic waves compared with effects of hyperthermia*. 9th International Congress of Biometerology (Osnabrueck, Allemagne), 23 septembre au 1$^{er}$ octobre 1981. Biometerology 8, part 1, p. 126, 127, septembre 1981.

PAUTRIZEL, R. & M$^{me}$ CHATEAUREYNAUD-DUPRAT, P. & M$^{lle}$ PAUTRIZEL, A. N. & MAYER, G. et PRIORE, A. (†) (1983). *Stimulation of protection mecanisms by magnetic fields and electromagnetic waves (Priore apparatus)*. First Symposium of the International Society of Bioelectricity (Boston, USA), 1$^{er}$ octobre 1983.

PÉRISSÉ, E. (1984). *Effets des ondes électromagnétiques et des champs magnétiques sur le cancer et la trypanosomiase expérimentale*. Thèse de doctorat en médecine, Bordeaux, n° 83, 16 mars 1984.

PEYCHÈS, I. (1978). *Qu'appelle-t-on phénomènes para-normaux ?*. Revue Sciences et Techniques, n° 50, avril 1978.

PRIORE, A. (1963). *Procédé et dispositif de production de rayonnements utilisables notamment pour le traitement de cellules vivantes*. Brevet d'invention, P.V. n° 899.414, N° 1.342.772, Classification internationale: A61 k-H05 g. Demandé le 1$^{er}$ juin 1962, Délivré par arrêté du 7 octobre 1963, Paris.

PRIORE, A. (1966). *Dispositif pour la production d'un rayonnement biologiquement actif*. Brevet d'invention, P.V. n° 78.512, N° 1.501.984, Classification internationale: A61n. Demandé le 3 octobre 1966, Délivré par arrêté du 9 octobre 1967, Paris.

RIVIÈRE, M. R. & PRIORE, A. & BERLUREAU, F. & FOURNIER, M. et GUÉRIN, M. (1964). *Action des champs électromagnétiques sur les greffes de la tumeur T8 chez le Rat*. Comptes rendus de l'académie des sciences (Paris), n° 259, groupe 14, p. 4895-4897, 21 décembre 1964.

RIVIÈRE, M. R. & CHOUROULINKOV, I. et GUÉRIN, M. (1965). *Etudes anatomo-pathologique et comportement biologique d'un lymphosarcome lymphoblastique transplantable du Rat associé à un syndrome leucémique*. Bulletin du cancer, t. 52, n° 2, p. 145-163, 1965.

RIVIÈRE, M. R. & PRIORE, A. & BERLUREAU, F. & FOURNIER, M. et GUÉRIN, M. (1965/02). *Effets de champs électromagnétiques sur un lymphosarcome lymphoblastique transplantable du Rat*. Comptes rendus de l'académie des sciences (Paris), n° 260, groupe 14, p. 2099-2102, 15 février 1965.

RIVIÈRE, M. R. & PRIORE, A. & BERLUREAU, F. & FOURNIER, M. et GUÉRIN, M. (1965/03). *Phénomènes de régression observés sur les greffes d'un lymphosarcome chez des souris exposées a des champs électromagnétiques*. Comptes rendus de l'académie des sciences (Paris), n° 260, groupe 14, p. 2639-2643, 1$^{er}$ mars 1965.

RIVIÈRE, M. R. et GUÉRIN, M. (1966). *Nouvelles recherches effectuées chez des rats porteurs d'un lymphosarcome lymphoblastique soumis à l'action d'ondes électromagnétiques associées à des champs magnétiques*. Comptes rendus de l'académie des sciences (Paris), t.262, série D, p. 2669-2672, 20 juin 1966.

<<La lueur>> (1973). Film d'information télévisuel FR3.

*Les machines de* PRIORE *ou le secret perdu*. Journal Sciences Frontières, 8 bis rue du chemin de fer, 94110 Arcueil, n° 12, octobre 1996.

M. PRIORÉ *s'inspire d'une théorie personnelle pour aider à la lutte contre le cancer*. Journal Sud-Ouest du 8 août 1952. <<*Je crois à la thérapeutique électronique*>> *affirme M.* PRIORÉ, *ingénieur, électronicien*. Journal Sud-Ouest du 16 août 1952.

CLINICAL REFERENCES

Our clinical development derives directly from our professional experience: the treatment of autistic and psychotic children.

Over a number of years, we tried to shine new light on this therapeutic work with these children which has enabled us to hear their essential need: their search for a continuity of being in a pacified, psychomatic globality.

This has led us to our own search for a global clinical approach.

Doctor Pierre LAFFORGUE, psychiatrist and psychoanalyst, Head of the Psychiatric Hospital in Bordeaux, has supervised the principal stages of this search. Through his mediation, Madame Geneviève HAAG, psychiatrist and psychoanalyst in Paris, has used the clinical observations we regularly supplied to lead—in a group consisting of psychiatrists, psychologists and psychoanalysts—a thorough exploration of autism through therapeutic work in the paddling pool; our experience was enhanced by this work.

If, in France, Madame G. HAAG's work in the field of autism is undeniably the most pertinent, that of Ms Frances TUSTIN, English psychiatrist and psychoanalyst, remains the most important reference. She came to Bordeaux a number of times and travels enormously to talk about her clinical work.

TUSTIN, F. (1977). *Autisme et psychose de l'enfant*. Le champ Freudien, Editions Le Seuil, Paris, 1977.

TUSTIN, F. (1986). *Les états autistiques chez l'enfant*. Editions Le Seuil, Paris, 1986.

TUSTIN, F. (1989). *Le trou noir le la psyché; Barrières autistiques chez les névrosés*. La couleur des idées, Editions Le Seuil, Paris, 1989.

TUSTIN, F. (1992). *Autisme et protection*. La couleur des idées, Editions Le Seuil, Paris, 1992.

The invention claimed is:

1. A device for stimulating the immune system of a living subject, animal or man, contained partly or in full in a volume of exposure, with diagnostic, preventive, therapeutic and biotechnological purposes, said device comprising:
   a) one or several generators, each producing an angle and amplitude modulated very high frequency signal,
   b) one or several applicators, each transforming said angle and amplitude modulated very high frequency signal into an angle and amplitude modulated very high frequency electromagnetic field in said volume of exposure, and varying the polarization of said angle and amplitude modulated very high frequency electromagnetic field,
   c) one or several magnetized masses producing a constant magnetic field in terms of time,
   or one or several conducting coils or superconductor coils producing a constant or variable magnetic field in terms of time in said volume of exposure,
   d) magnetic circuits, associated with the coils or magnetized masses, presenting air gaps between pole pieces of the magnetic circuits; said pole pieces of the magnetic circuits being positioned around said volume of exposure, and
   e) a structure or a structure receptacle and envelope surrounding the volume of exposure, and containing said one or several applicators and said pole pieces of the magnetic circuits.

2. The device according to claim 1 wherein each of said one or several generators comprises:
   a) an oscillator generating a sinusoidal very high frequency carrier signal,
   b) an angle modulator with a generator producing an angle modulation signal; said angle modulation signal controlling said angle modulator; said very high frequency carrier signal being angle-modulated by said angle modulator,
   c) an amplitude modulator with a generator producing an amplitude modulation signal; said amplitude modulation signal controlling said amplitude modulator; said very high frequency carrier signal being amplitude-modulated by said amplitude modulator, and
   d) an amplifier to amplify said very high frequency carrier signal being angle-modulated and amplitude-modulated, in order to produce said angle and amplitude modulated very high frequency signal.

3. The device according to claim 2 wherein said sinusoidal very high frequency carrier signal has a frequency between 1 GHz and 20 GHz.

4. The device according to claim 2 wherein said angle modulation signal being periodic and has a frequency spectrum between 10 MHz and 300 Mhz; the angle modulation index of said angle and amplitude modulated very high frequency signal is greater than or equal to $\pi/4$.

5. The device according to claim 2 wherein said amplitude modulation signal is periodic and has a frequency spectrum between 1 KHz and 1 MHz.

6. The device according to claim 1 wherein each of said one or several applicators, comprises:
   a) a two-way power splitter which separates said angle and amplitude modulated very high frequency signal into two branches,
   b) a phase shifter in one branch to shift the phase of said modulated very high frequency signal compared to the phase of said modulated very high frequency signal in the other branch,
   c) an amplitude modulator in each branch to vary the amplitude of said modulated very high frequency signal in each branch,
   d) an amplifier in each branch,
   e) an array of radiating elements for each branch in order to convert said modulated very high frequency signal into said modulated very high frequency electromagnetic field with a linear polarization; both of said array of radiating elements being arranged so that the polarization of the electromagnetic field of a branch is orthogonal to the polarization of the electromagnetic field of the other branch, and
   f) a generator producing low frequency modulation signals which control said amplitude modulator in each branch and said phase shifter.

7. The device according to claim 1 wherein said polarization of said angle and amplitude modulated very high frequency electromagnetic field is linear and/or elliptic oriented right or left, and/or circular oriented right or left; the angle of said polarization varying continuously or discretely with a uniform probability density.

8. The device according to claim 1 wherein said one or several conducting coils or superconductor coils producing a constant or variable magnetic field in terms of time are fed by a release/recovery generator which produces a constant or variable current in terms of time and which comprises a bridge with:
   a) a first pair of thyristors, arranged on two opposite branches of the bridge, in order to discharge into said one or several conducting coils or superconductor coils a capacitor charged previously by means of a subsidiary supply,
   b) a current maintaining supply, in said one or several conducting coils or superconductor coils to take over when the capacitor is discharged,
   c) a second pair of thyristors or a pair of diodes, arranged on the two opposite branches of the bridge, in order to recover electrically into the capacitor the magnetic energy stored in said one or several conducting coils or superconductor coils when the maintaining supply stops.

9. The device according to claim 8 wherein the variation of said constant or variable current is periodic and has a frequency spectrum between 0 and 100 Hertz.

10. The device according to claim 1 wherein said structure receptacle and envelope is of a circular shape, on a vertical axis, of a diameter of 2.5 m, with rounded contours, surmounted by a transparent dome and is capable of being placed on a floor;
   partitions divide said structure receptacle and envelope into compartments; the partitions are vertical and aligned according to radius of the said structure receptacle and envelope, leaving a circular space of 1 meter in diameter;
   the partitions contain said pole pieces in order to apply said magnetic field in the compartments;
   each compartment has one opening or one passage way communicating with the outside of said structure receptacle and envelope;
   said one or several magnetized masses, said one or several conducting coils or superconductor coils, and said magnetic circuits being placed under said floor;
   said one or several applicators are arranged in the compartments.

11. Use of the device according to claim 1 for stimulating the immune system of an animal in order to obtain polyclonal or monoclonal antibodies from said animal for stimulating said immune system, said animal being placed in the volume of exposure during 2 to 4 hours per day.

12. Use of the device according to claim 1 for a preventive or therapeutic treatment of animal or man; to perform said treatment, said animal or man is placed in the volume of exposure during 1 to 2 hours per day.

* * * * *